(12) United States Patent
Dames

(10) Patent No.: US 6,577,237 B1
(45) Date of Patent: Jun. 10, 2003

(54) UNI-DIRECTIONAL MAGNETIC TAG

(76) Inventor: Andrew Nicholas Dames, 74 De Freville Avenue, Cambridge CB4 1HU (GB)

( * ) Notice: Subject to any disclaimer, the term of this patent is extended or adjusted under 35 U.S.C. 154(b) by 0 days.

(21) Appl. No.: 09/582,851

(22) PCT Filed: Jul. 15, 1999

(86) PCT No.: PCT/GB99/00017

§ 371 (c)(1),
(2), (4) Date: Aug. 21, 2000

(87) PCT Pub. No.: WO99/35516

PCT Pub. Date: Jul. 15, 1999

(30) Foreign Application Priority Data

Jan. 5, 1998 (GB) ............................................. 9800064

(51) Int. Cl.[7] ............................................... G08B 13/14
(52) U.S. Cl. ..................... 340/572.1; 340/551; 148/300
(58) Field of Search .............................. 340/551, 572.1; 148/300

(56) References Cited

U.S. PATENT DOCUMENTS

| 4,710,754 A | * 12/1987 | Montean ...................... 340/572 |
| 4,746,908 A | * 5/1988 | Montean ...................... 140/551 |
| 5,057,095 A | 10/1991 | Fabian ......................... 604/362 |

FOREIGN PATENT DOCUMENTS

| EP | 0 406 004 A2 | 2/1991 |
| EP | 0 628 936 A1 | 12/1994 |
| WO | WO 92/07343 | 4/1992 |

* cited by examiner

*Primary Examiner*—John Sheehan
(74) *Attorney, Agent, or Firm*—Oppenheimer Wolff & Donnelly LLP

(57) ABSTRACT

A uni-directional tag for use with position and orientation detection systems, which is not affected by exposure to high magnetic field levels. The tag is constructed from special geometry of magnetic materials and is applicable for example to catheter location systems.

14 Claims, 3 Drawing Sheets

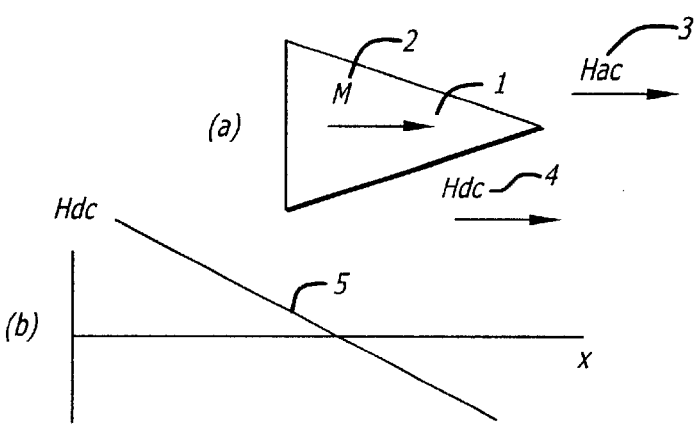
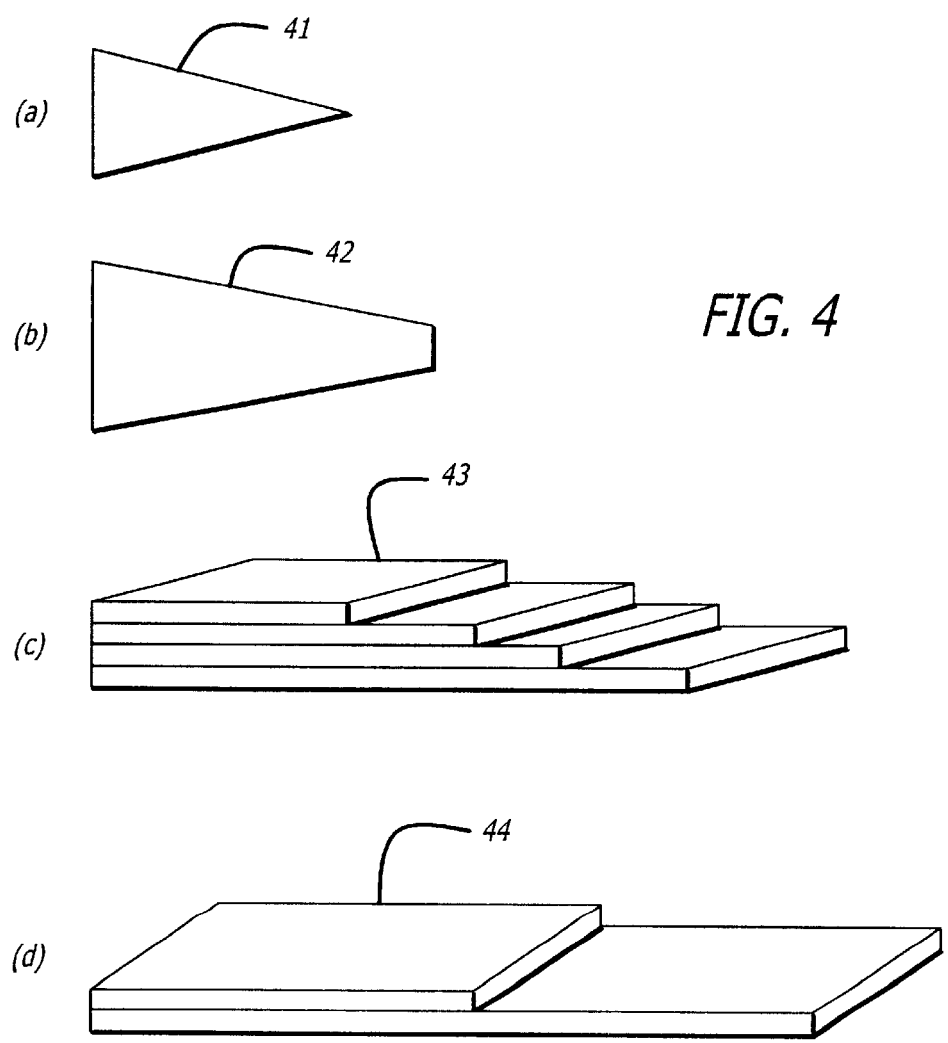

FIG. 3a
FIG. 3b
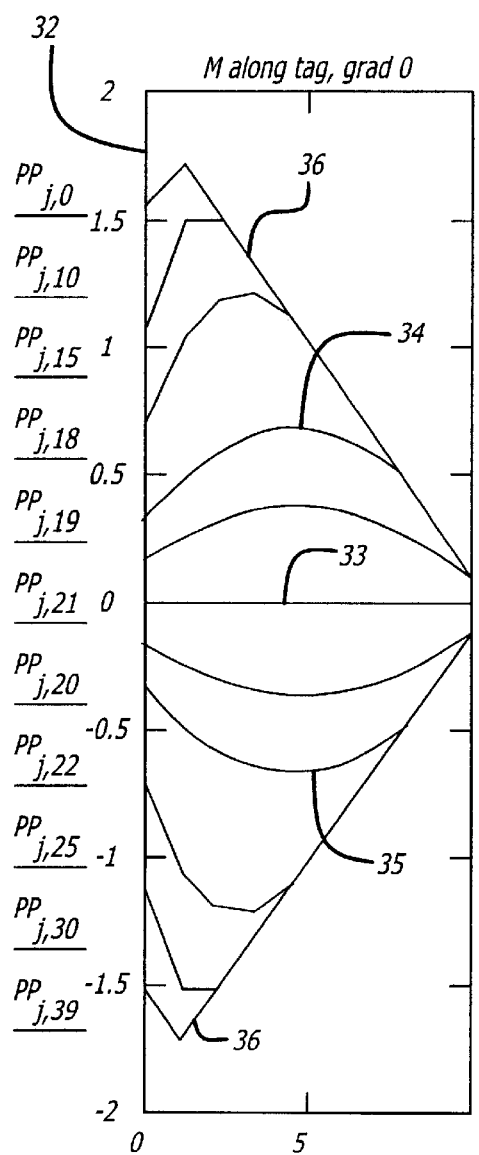
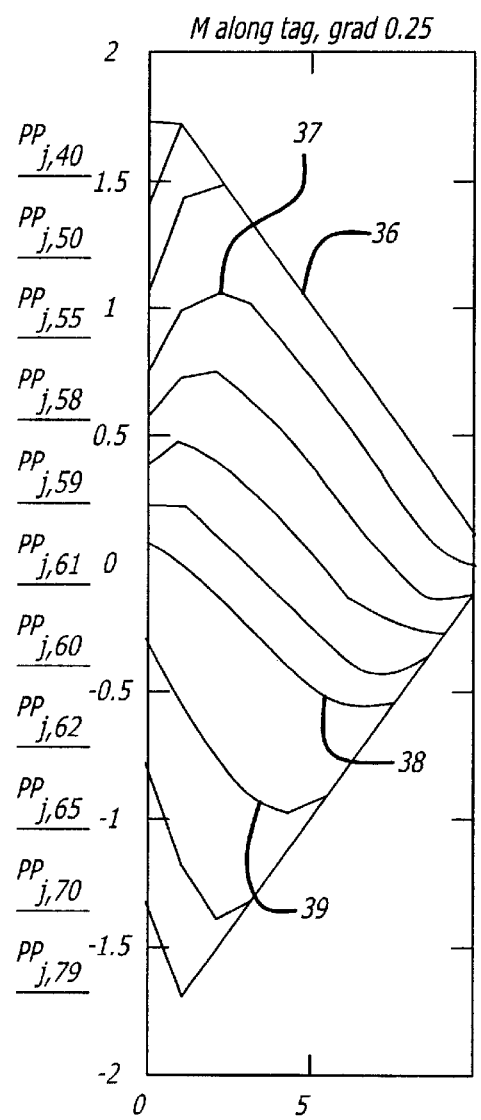

UNI-DIRECTIONAL MAGNETIC TAG

This invention relates to a magnetic marker or tag and to methods of position and orientation detection using the marker or tag. It will be appreciated that the terms "marker" and "tag" are used herein interchangeably; the term "label" is also used in the art to describe magnetic articles of the type to which this invention relates. It should also be noted that the term "magnetic" is used herein in the sense that the tag undergoes some kind of detectable change when subjected to appropriate magnetic conditions; the term does not imply that the tag is ferromagnetic—in general, the tag will not display ferromagnetic properties. Typically, the magnetic materials used for such tags are soft magnetic materials; these may display anisotropic magnetic properties, usually possessing a preferred direction of magnetisation—i.e. an axis along which the material may readily be magnetised; the magnetic permeability along this preferred axis is much greater than in other directions.

A tag in accordance with this invention can be added to existing equipment, for instance it may be secured to the tip of a catheter, which is used in conjunction with special interrogation equipment. The essence of the invention is the provision of a uni-directional tag, which avoids the 180 degree ambiguity usually found with the existing state-of-the-art magnetic tags.

EAS (electronic article security) systems use a magnetic material as a marker or tag, which is attached typically to retail articles. Typically the tag is detected by a pair of coils when the tag passes between them. These EAS systems utilise the magnetic (induction) characteristics of the material used in the tag for the purpose of detection.

A more advanced system is able to detect not only the presence but also the location and orientation of the tag or market. An example of an application where this is beneficial would be catheter location, where the magnetic material (tag) can be directly sputtered onto existing catheters. The position and orientation of the catheter can then be determined using external systems.

Existing tags have suffered from being bi-directional; that is their orientation is ambiguous since the detection signal is the same after rotating the tag through 180 degrees as it was initially. Thus the presence of the tag may readily be detected, but its orientation is undefined since it could be positioned in either of two possible pointing directions.

Alternatively the tags have incorporated hard magnetic material, which can be affected by large external field levels and the tag performance is then deranged.

The invention provides a tags which has been designed so that in the presence of a magnetic gradient field, it exhibits a non-symmetric MH loop. Hence the pointing direction of the tag can be detected. (Note—it is customary to describe magnetic material properties as "BH" loop, whereas this patent will describe the MH loop, where M is magnetisation).

According to one aspect of the present invention there is provided a tag which is characterised in that the saturation magnetisation of the tag material is not a constant value at all points along the tag.

This invention describes a tag whose orientation is unambiguous and includes features that the interrogation equipment can process to yield pointing direction. The tag can be constructed so that it can survive exposure to high magnetic fields typically found in MRI (magnetic resonance imaging) machines without affecting its unidirectional behaviour. Thus the tag is generally formed of a material which does not undergo permanent change when exposed to high magnetic fields.

Generally, the tag has a main axis and in that the saturation magnetisation at one end of said axis differs from the saturation magnetisation at the opposite end of said axis. Conveniently, the saturation magnetisation is a function of position along said axis. One way of achieving this is for the tag to be tapered in shape. For example, the tag may be triangular in cross-section. In one embodiment, the tag is generally elongate and is wider at one end than at the other. In another embodiment, the tag is generally elongate and has a thickness which is greater at one end than at the other. A tag of this form may be constructed by laminating material to achieve variation in thickness. In a third embodiment, the tag is generally elongate and is tapered in both the width and thickness directions.

A tag in accordance with this invention may be formed from a spin melt ribbon or from thin film material. Alternatively, the tag is formed from thin mu-metal sheet.

It is also possible to make the tag by sputtering a material directly onto a carrier whose position is to be detected.

Certain specific embodiments of the invention will now be described by way of example with reference to the accompanying drawings in which:

FIG. 1(a) shows the physical form of one embodiment of the uni-directional tag of this invention;

FIG. 1(b) illustrates a magnetic field gradient;

FIG. 3 is a graph illustrating the magnetisation field levels generated along the tag length for various applied field gradients; and FIG. 4 illustrates several alternative embodiments of the invention.

FIG. 1 illustrates on e embodiment of the tag and the method of interrogation used with the tag, which yields uni-directional behaviour. The tag, 1, consists of a soft magnetic material such as 6025 material from Vacuumschmeltze, Germany, of uniform thickness and designed to be tapered in width. The figures indicates a structure which is tapered to a point; however a rhomboid would also function satisfactorily. The tag is interrogated by a longitudinal alternating magnetic field (Hac), 3. Simultaneously a longitudinal DC magnetic field gradient, 4, whose strength varies linearly with longitudinal position is applied. The field gradient versus longitudinal position is illustrated by the graph 5 of FIG. 1(b). The longitudinal direction refers to the direction along the tag illustrated. The DC fields may be generated with permanent magnets or alternatively coils of wire carrying DC current. The AC field can be generated usually with coils of wire and AC currents. The applied field is a function of time and position and induces in the tag a magnetisation flux M, 2. The total tag magnetisation M can be detected by externally arranged coils and the behaviour of the tag may be measured in a magnetometer instrument. These devices are designed to measure B-H (M-H) loop characteristics of materials. The measured tag magnetisation M is a function of the magnetic material used and the tag shape.

Figure 2A:
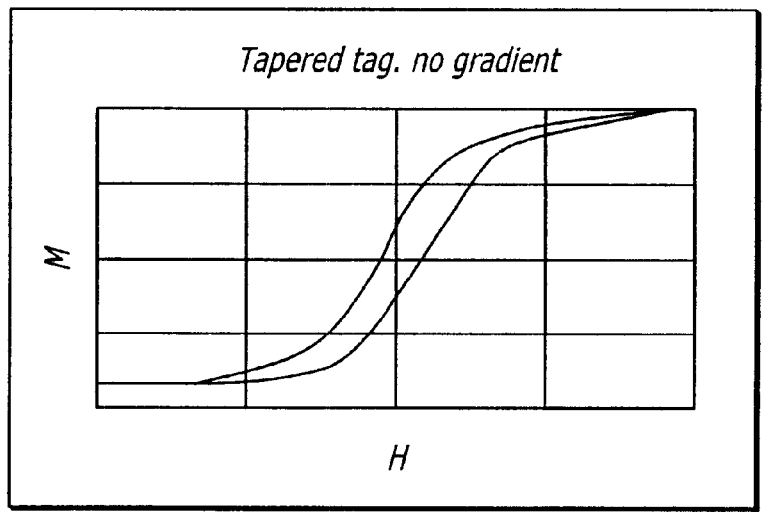
FIG. 2 illustrates the non-symmetric-M-H loop measurement generated by this tag.
Figure 2B:
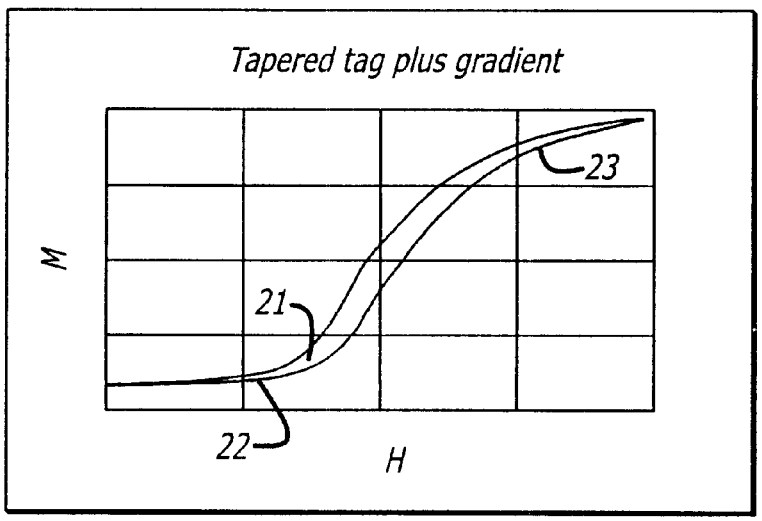

The tag's measured behaviour is illustrated by FIG. 2. FIG. 2a shows the M-H loop for the tag when the DC field gradient is zero and shows the response to the AC field component. The loop is symmetric and therefore if the tag was turned through 180 degrees in the magnetometer measuring its characteristics, the measured loop will look identical. FIG. 2b illustrates the measured behaviour with a DC field gradient applied. The characteristic is not symmetric and if the tag is turned through 180 degrees in the magnetometer then the M-H loop would be mirrored in the vertical axis. Hence it is possible to determine the tag orientation.

FIG. 3 shows the results of the magnetic field modelling for the tag and illustrates the features that cause the tag to exhibit unidirectional behaviour. FIG. 3a illustrates tag magnetisation versus longitudinal position plotted for an applied AC field component as a parameter with zero applied DC field gradient. Referring to FIG. 3a, the x-axis, 31, represents position along the tag; the y-axis, 32, represents the magnetisation M in a tag element at that position. The line 33 represents the graph for zero applied AC magnetic field amplitude. Lines 34 and 35 represent positive and negative peak amplitudes of the applied AC field as parameters. The line 36 parameter represents where the magnetic material saturates in the tag and the magnetisation is the maximum allowed by the material. The value shown varies from zero at the pointed end of the tag to a value of two (arbitrary units) at the widest point of the tag, and is a function of the available material volume along the tag length. FIG. 3a illustrates tag magnetisation versus longitudinal position plotted for an applied AC field component as a parameter with zero applied DC field gradient. Note that the behaviour is symmetric and specifically that for positive and negative (34 and 35) peak AC field values, magnetisation at any arbitrary position have the same magnitude.

FIG. 3b illustrates the tag behaviour under the influence of an applied DC field gradient. For positive and negative peak applied AC field levels (37 and 38), the magnetisation is now not symmetric. Specifically it can be seen that the position along the tag where saturation is reached differs depending on the direction (polarity) of the applied AC field. In FIG. 3b, line 37 illustrates that saturation is never achieved, whereas line 38 illustrates that the tag saturates at the pointed end and then comes out of saturation further along the tag. The non-symmetric effect illustrated by FIG. 3b is one way of explaining the non-symmetric M-H behaviour of the tag.

The relationship between FIG. 3b, the tag magnetisation, and FIG. 2b, the non-symmetric M-H loop is explained below. Referring to the magnetisation along the tag illustrated by the lines 37 and 38 it may be seen that as the AC magnetic field amplitude is increased, line 38 moves towards 39. The tag magnetisation versus applied (positive) peak AC field increases but is limited by saturation in the material. This corresponds to the portion of the MH loop illustrated by 23 in FIG. 2b. As AC field (negative peak value) applied in the opposite direction (shown by the line 37 in FIG. 3b and approximately corresponding to the point 21 as shown in FIG. 2b) is increased it will intercept with the saturation level 36. The tag magnetisation cannot increase much further as is illustrated by point 22 in FIG. 2b.

The model also illustrates that non-symmetric behaviour can be achieved by alternative tag forms. Examples of these are shown in FIG. 4. In FIG. 4(a), the tag, 41, is as described in FIG. 1. It is constructed from 6025 material (see below) 25 micron thick, 5mm wide and 30mm long. An alternative, 42, is shown in FIG. 4(b). In FIG. 4(c), the tag 43, is constructed from several layers of 6025 material, 0.5mm wide, 25 micron thick and 30mm long. This achieves a tapered thickness. The same can be achieved with thin film materials. These comprise a thin (1 micron) layer of magnetic material deposited on a plastic film (which may, for example, be 23 microns thick). Tag 44 of FIG. 4(d) illustrates this with only two pieces of the thin film material "Atalante" and is 5mm wide by 10mm long.

Appropriate field levels used for the tag illustrated in FIG. 1 are an AC component of +/−400 A/m and a DC field gradient of 15kA/m/m. The AC frequency used was 1kHz although the thin film materials described are capable of good performance up to 10–20 kHz.

Further alternatives may be constructed by varying the material magnetic properties with longitudinal position. Specifically varying $M_{sat}$ (the saturation magnetisation) with longitudinal position will yield the desired result.

Thin film magnetic materials, where the magnetic material is sputtered onto for instance PET film, are manufactured by IST of Zulte Belgium under the trade name Atalante. Ribbon magnetic materials are manufactured by Vacuumschmeltze of Hanau, Germany. They are marketed under a trade name of VitroVac and a suitable type is 6025. Neither of these materials are deranged by exposure to very high magnetic field levels (i.e. of a few Tesla).

The tag may typically be used as part of a catheter location system. The tag will be mounted on the tip of the catheter. An external interrogation device detects the orientation of the tag and displays this to the operator. Processing of the M-H loop characteristics to yield orientation is obvious to those experienced in the art of signal processing.

What is claimed is:

1. A tag which is characterized in that said tag has a main axis and in that the saturation magnetization at one end of said axis differs from the saturation magnetization at the opposite end of said axis, such that when interrogated by an alternating magnetic field while simultaneously applying a direct magnetic gradient field, the orientation of the tag in a given direction X can be distinguished from the orientation of the tag in a direction X+180 degrees.

2. A tag as claimed in claim 1, characterised in that the saturation magnetisation is a function of position along said axis.

3. A tag as claimed in claims 1, characterised in that the tag is tapered in shape.

4. A tag as claimed in claim 1, characterised in that the tag is triangular in cross-section.

5. A tag as claimed in claim 3, characterised in that the tag is generally elongate and is wider at one end than at the other.

6. A tag as claimed in claim 3, characterised in that the tag is generally elongate and has a thickness which is greater at one end than at the other.

7. Tag according to claim 6, characterised in that the tag is constructed from laminating material to achieve variation in thickness.

8. A tag as claimed in claim 3, characterised in that the tag is generally elongate and is tapered in both the width and thickness directions.

9. A tag as claimed in claim 1, characterised in that the tag is formed from a spin melt ribbon.

10. A tag as claimed in claim 1 characterized in that the tag is formed from thin film material.

11. A tag as claimed in claim 1 characterized in that the tag is formed from thin mu-metal sheet.

12. A tag as claimed in claim 1 characterized in that the tag is made by sputtering a material directly onto a carrier whose position is to be detected.

13. A method of determining the orientation of an object, comprising the steps of (1) providing the object with a tag having a main axis, wherein the saturation magnetization at one end of said axis differs from the saturation magnetization at the opposite end of said axis;

(2) applying an interrogation field comprising an alternating magnetic field together with a direct gradient field to the region which the object is located; and (3) detecting the response of the tag to the interrogation field.

14. A method as claimed in claim 13, wherein the object is a catheter.

* * * * *

UNITED STATES PATENT AND TRADEMARK OFFICE
CERTIFICATE OF CORRECTION

PATENT NO.      : 6,577,237 B1
DATED           : June 10, 2003
INVENTOR(S)     : Andrew Nicholas Dames It is certified that error appears in the above-identified patent and that said Letters Patent is hereby corrected as shown below:

<u>Title page,</u>
Item [22], PCT Filing Date is corrected to read, -- January 5, 1999. --

Signed and Sealed this

Fourteenth Day of October, 2003

JAMES E. ROGAN
*Director of the United States Patent and Trademark Office*